(12) United States Patent
Tanaami

(10) Patent No.: US 7,466,408 B2
(45) Date of Patent: Dec. 16, 2008

(54) MEASUREMENT SYSTEM

(75) Inventor: Takeo Tanaami, Musashino (JP)

(73) Assignee: Yokogawa Electric Corporation, Tokyo (JP)

( * ) Notice: Subject to any disclaimer, the term of this patent is extended or adjusted under 35 U.S.C. 154(b) by 11 days.

(21) Appl. No.: 10/287,658

(22) Filed: Nov. 5, 2002

(65) Prior Publication Data

US 2003/0095254 A1 May 22, 2003

(30) Foreign Application Priority Data

Nov. 21, 2001 (JP) .............................. 2001-355843

(51) Int. Cl.
| | |
|---|---|
| *G01J 3/30* | (2006.01) |
| *G01J 1/58* | (2006.01) |
| *G01N 21/85* | (2006.01) |
| *F21V 9/16* | (2006.01) |
| *G01T 1/10* | (2006.01) |
| *G21H 3/02* | (2006.01) |
| *G21K 5/00* | (2006.01) |
| *H01J 65/06* | (2006.01) |
| *H01J 65/08* | (2006.01) |
| *H01J 3/14* | (2006.01) |
| *H01J 5/16* | (2006.01) |
| *H01J 40/14* | (2006.01) |

(52) U.S. Cl. .................... 356/317; 356/417; 250/458.1; 250/234

(58) Field of Classification Search ................. 356/317, 356/417, 436, 440; 250/458.1
See application file for complete search history.

(56) References Cited

U.S. PATENT DOCUMENTS

| | | | |
|---|---|---|---|
| 4,723,846 A * | 2/1988 | Uehara et al. | |
| 4,798,965 A * | 1/1989 | Fetzer et al. | 250/573 |
| 5,120,953 A * | 6/1992 | Harris | 250/227.2 |
| 5,233,197 A * | 8/1993 | Bowman et al. | 250/461.1 |
| 5,394,271 A * | 2/1995 | Tanaka et al. | |
| 5,422,872 A * | 6/1995 | Hsu et al. | 369/97 |
| 5,459,325 A * | 10/1995 | Hueton et al. | 250/458.1 |
| 5,528,050 A * | 6/1996 | Miller et al. | 250/585 |
| 5,574,712 A * | 11/1996 | Alon et al. | 369/102 |
| 5,713,364 A * | 2/1998 | DeBaryshe et al. | 600/476 |
| 5,729,385 A * | 3/1998 | Nishida et al. | |
| 5,854,487 A * | 12/1998 | Braunstein et al. | 250/306 |
| 5,880,465 A * | 3/1999 | Boettner et al. | |
| 5,900,640 A * | 5/1999 | Ogura | 250/583 |
| 5,900,949 A * | 5/1999 | Sampas | 358/482 |
| 6,093,370 A * | 7/2000 | Yasuda et al. | 422/68.1 |
| 6,100,535 A * | 8/2000 | Mathies et al. | 250/458.1 |
| 6,134,002 A * | 10/2000 | Stimson et al. | 356/326 |

(Continued)

FOREIGN PATENT DOCUMENTS

JP          5-60980          3/1993

(Continued)

Primary Examiner—Michael A Lyons
Assistant Examiner—Gordon J Stock, Jr.
(74) Attorney, Agent, or Firm—Westerman, Hattori, Daniels & Adrian, LLP.

(57) ABSTRACT

A measurement system that optically measures in turn a plurality of samples arranged in an array via an objective lens and an imaging lens is disclosed, which is characterized by comprising an actuator means that moves the above described objective lens corresponding to each position of the above mentioned samples, and a photo-detecting part that detects a sample image via the above objective lens and imaging lens.

9 Claims, 6 Drawing Sheets

U.S. PATENT DOCUMENTS

| | | | |
|---|---|---|---|
| 6,172,785 B1 * | 1/2001 | Wulf | 359/196 |
| 6,278,682 B1 * | 8/2001 | Takishima et al. | 369/119 |
| 6,297,904 B1 * | 10/2001 | Kitagawa et al. | |
| 6,329,661 B1 * | 12/2001 | Perov et al. | 250/461.2 |
| 6,335,824 B1 * | 1/2002 | Overbeck | 359/368 |
| 6,355,934 B1 * | 3/2002 | Osgood et al. | 250/458.1 |
| 6,545,264 B1 * | 4/2003 | Stern | 250/234 |
| 6,548,796 B1 * | 4/2003 | Silvermintz et al. | 250/201.3 |
| 6,563,581 B1 * | 5/2003 | Oldham et al. | 356/317 |
| 6,577,394 B1 * | 6/2003 | Zavislan | 356/369 |
| 6,674,574 B1 * | 1/2004 | Aono | 359/383 |
| 6,762,840 B1 * | 7/2004 | Kimura | 356/417 |
| 6,775,002 B2 * | 8/2004 | Nawracala | 356/440 |
| 6,850,362 B2 * | 2/2005 | Brooker | 359/379 |
| 7,236,251 B2 * | 6/2007 | Takaoka | 356/497 |
| 2001/0048082 A1 * | 12/2001 | Osipchuk et al. | 250/458.1 |
| 2002/0139936 A1 * | 10/2002 | Dumas | 250/458.1 |
| 2002/0163717 A1 * | 11/2002 | Lee | 359/388 |
| 2003/0142309 A1 * | 7/2003 | Kuebler et al. | 356/338 |

FOREIGN PATENT DOCUMENTS

| | | |
|---|---|---|
| JP | 9-61719 | 3/1997 |
| JP | 2000121559 | 4/2000 |
| JP | 2000329769 | 11/2000 |

\* cited by examiner

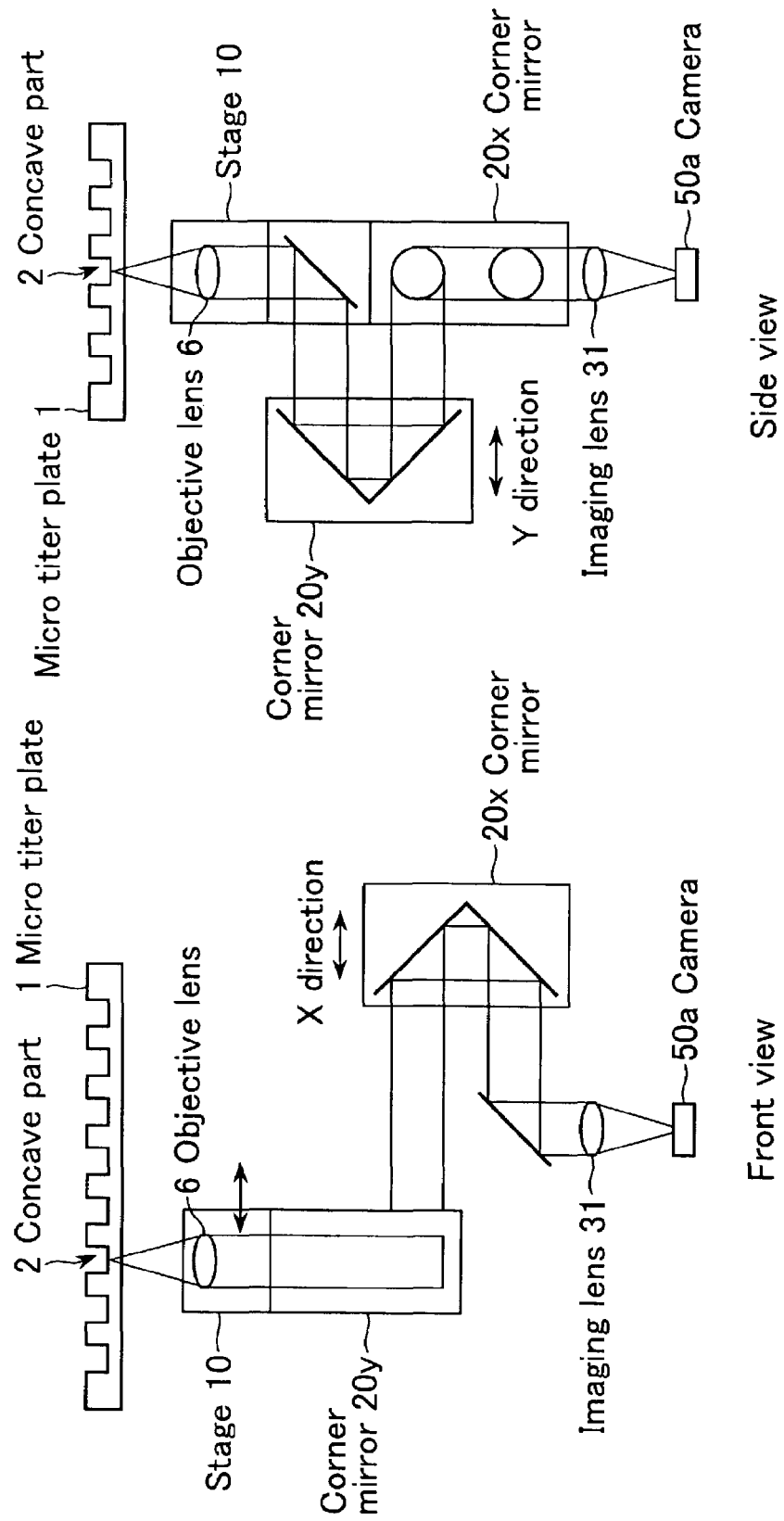
FIG.4B Side view
FIG.4A Front view

MEASUREMENT SYSTEM

BACKGROUND OF THE INVENTION

1. Field of the Invention

The present invention relates to the improvement of measurement systems in which samples such as living cells arranged in a two-dimensional array are measured.

2. Description of the Prior Art

FIG. 1 is a configuration drawing indicating the essential parts of an example of conventional measurement systems of this type.

In FIG. 1, concave parts 2 are provided in a two-dimensional array on micro titer plate 1 made of a transparent material or materials, and solutions containing samples such as living cells are put in these concave parts.

The exciting light beam from light source 3 is made parallel with lens 4, reflected by dichroic mirror 5, and incident to objective lens 6. The exciting light which is stopped down with objective lens 6 irradiates a sample in one of the concave parts 2 of micro titer plate 1. Fluorescence generated from the sample due to excitation by the exciting light is transmitted through dichroic mirror 5 after passing through objective lens 6 and is reflected by reflection mirror 7 and incident to imaging lens 8. The light that has been transmitted through lens 8 hits the image detecting plane of camera 9 and the sample image is formed here.

When each sample in each of concave parts 2 is to be observed by scanning them, images of each sample are obtained in turn by moving micro titer plate 1 in the horizontal direction (in the figure, back and forth and in the right and left direction on the paper surface) with a mechanism not shown in FIG. 1, without moving the optical system. Such a system is very useful, for example, to measure reactions of various living cells to pharmaceuticals.

In order to increase the speed of such a system, the micro titer plate must be moved rapidly. In this case, there are the following problems:

(1) Solutions may slosh out of the concave parts as shown in FIG. 2.
(2) It is not easy to move micro titer plate 1 because it is large and has a great inertial force.

SUMMARY OF THE INVENTION

The purpose of the present invention is to solve the above described problems thereby realizing a measurement system which enables various samples to be measured by scanning them at a high speed with fixed samples and a mobile objective lens system, the measurement system optically measuring a plurality of samples arranged in an array via the objective lens and the imaging lens.

BRIEF DESCRIPTION OF THE DRAWINGS

FIG. 4 is a configuration drawing indicating the essential parts of another embodiment of the present invention.

DETAILED DESCRIPTION OF THE PREFERRED EMBODIMENTS

Figure 1:
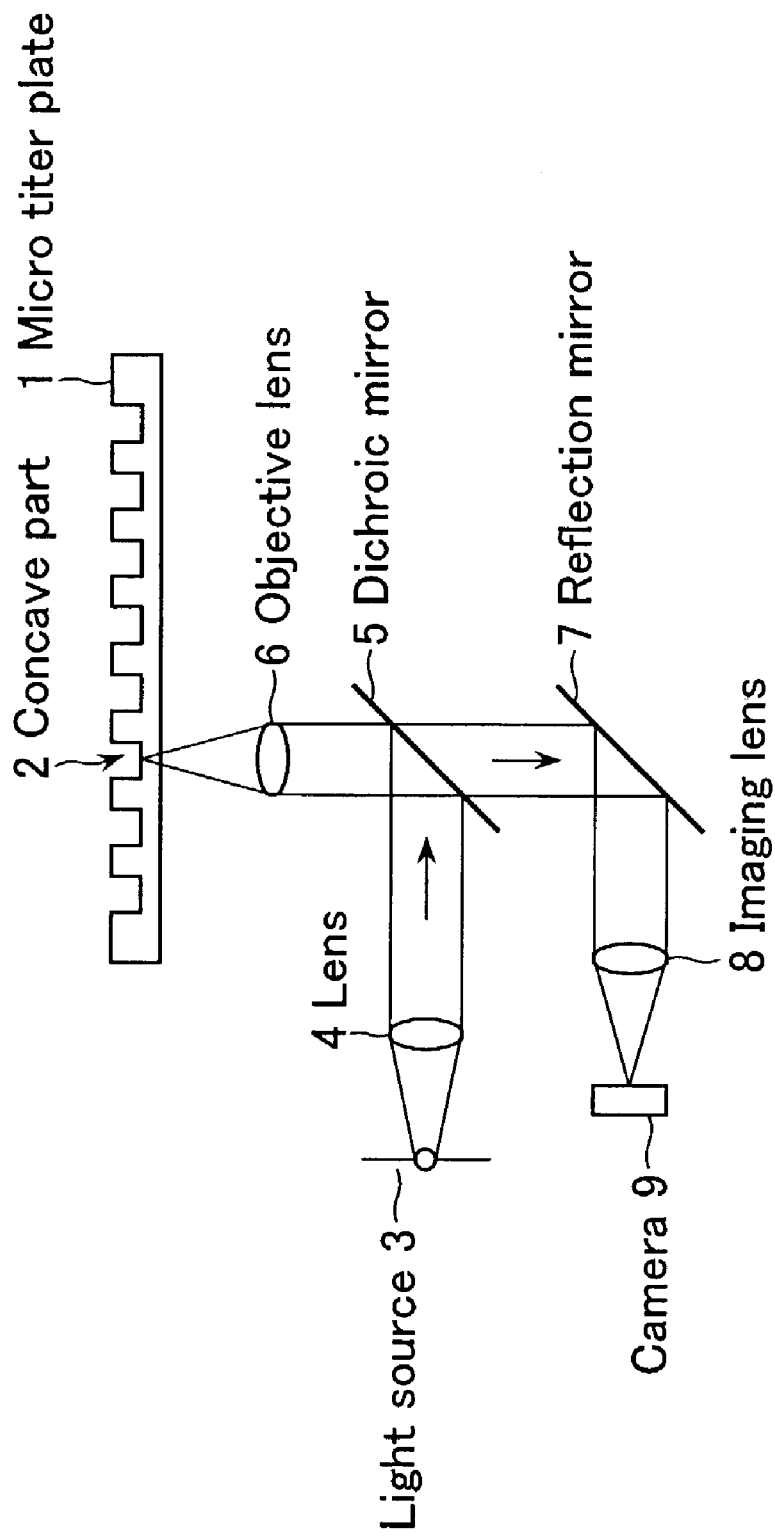
FIG. 1 is a configuration drawing indicating the essential parts of an example of conventional high-throughput screening systems.
Figure 2:
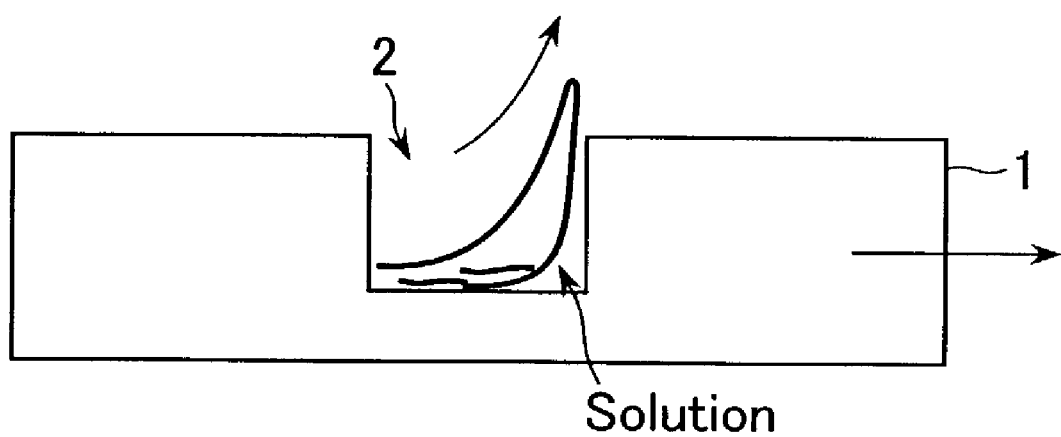
FIG. 2 is a drawing showing that the solution sloshes out of a micro titer plate in conventional systems.
Figure 3:
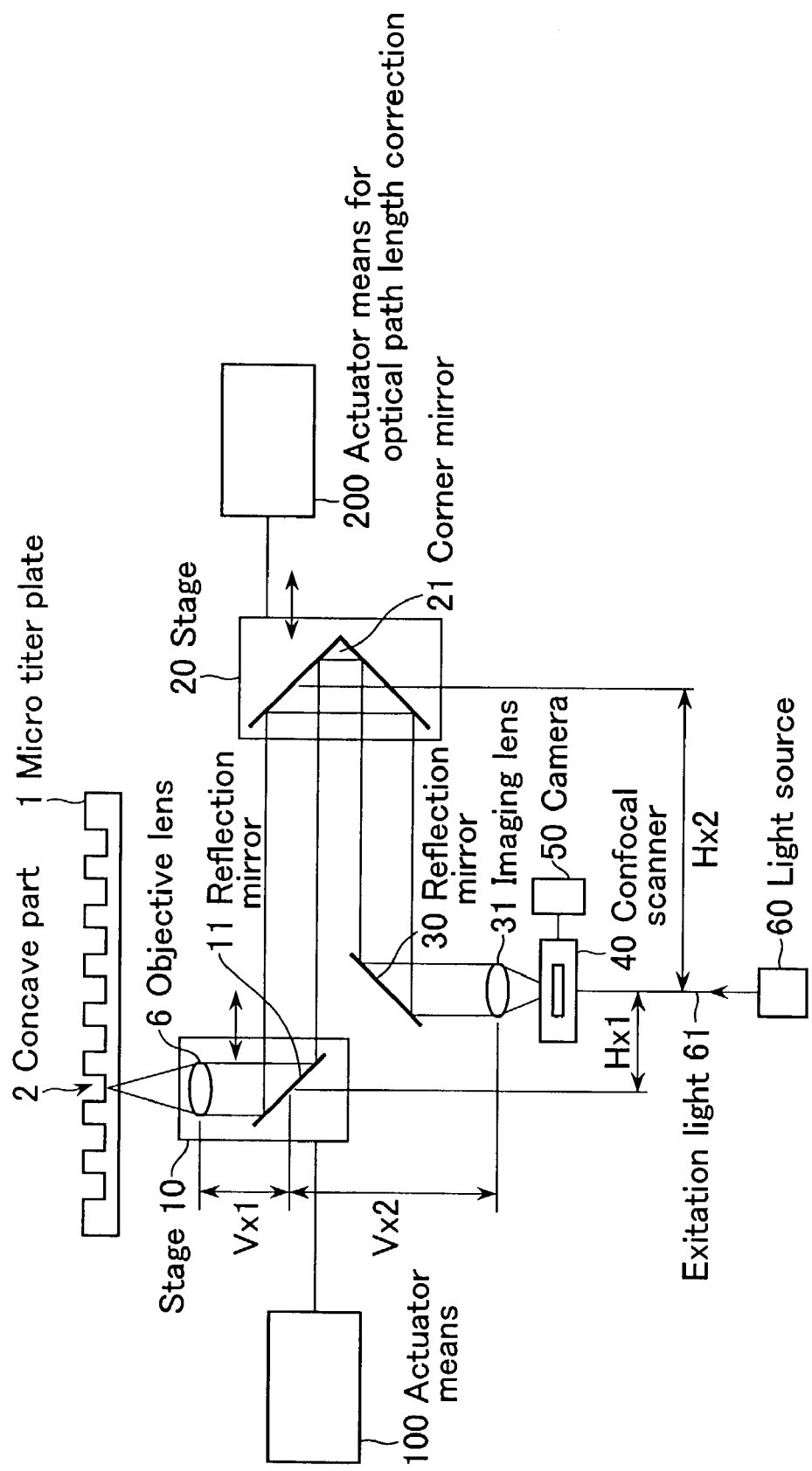
FIG. 3 is a configuration drawing indicating the essential parts of an embodiment of the measurement system based on the present invention.

The present invention will be described below in detail using drawings. FIG. 3 is a configuration drawing indicating the essential parts of an embodiment of the measurement system based on the present invention. In addition, FIG. 3 is the configuration drawing in the case where the telecentric distance is intended to be constant corresponding to the movement of objective lens 6.

In FIG. 3, number 10 shows the first stage, to which objective lens 6 and reflection mirror 11 are mounted, and which is freely movable in the direction orthogonal to the optical axis, and number 20 shows the second stage, to which corner mirror 21 is mounted, and which is freely movable in the direction parallel to the moving direction of first stage 10.

Number 30 shows a reflection mirror, number 31 an imaging lens, number 40 a confocal scanner, number 50 a camera, number 60 a light source that generates the excitation light, number 100 an actuator means for moving stage 10, and number 200 an actuator means for optical path length correction.

Further, the part comprising confocal scanner 40 and camera 50 is hereupon called the photo-detection part.

Excitation light 61 from light source 60 is incident to imaging lens 31 after passing through confocal scanner 40. The excitation light made parallel by imaging lens 31 is reflected by reflection mirror 30 and incident to corner mirror 21. The excitation light emitted from corner mirror 21 due to folding-back is incident to objective lens 6 after its direction is turned at reflection mirror 11. The excitation light focused with objective lens 6 irradiates the samples on micro titer plate 1.

Light emitted from the samples excited by the excitation light (hereinafter called the return light from the sample) traces the optical path in the direction opposite to the incident light and thus is incident to confocal scanner 40 via objective lens 6, reflection mirror 11, corner mirror 21, reflection mirror 30 and imaging lens 31.

As confocal scanner 40, for example, the confocal scanner, which is disclosed in Japanese Patent Application Laid-Open No. 5-60980 proposed by the applicant for the application concerned, can be used. Confocal scanner 40 is constituted so that the excitation light is transmitted to the sample side through pinholes in the pinhole substrate (not shown) and the return light from the samples as well is again returned through the pinholes.

Light returned through the pinholes forms images on the image-detecting plane of camera 50 via a branching optical system (not shown).

In this case, if the pinhole substrate is rotated at a constant speed, positions of pinholes are moved and the sample surface is optically scanned with focusing light spots. This enables the image of the sample surface to be observed with camera 50.

In such a configuration, micro titer plate 1, reflection mirror 30, lens 31, confocal scanner 40, camera 50 and light source 60 are fixed and only first stage 10 and second stage 20 are mobile.

Each stage is moved by actuator means 100 and actuator means for optical path length correction 200 respectively. In the present invention, the following relationship is maintained in this case.

In the present invention, the stages are moved with the optical path length kept constant, which is the distance from objective lens 6 to lens 31, that is, so-called telecentric distance L. Unless distance L is kept constant, a detrimental influence occurs, in which the quantity of light becomes insufficient at the periphery of the screen as mentioned in Japanese Patent Application Laid-Open No. 9-61719 "Confocal Microscope" proposed by the applicant for the application concerned.

Now assume that, as shown in FIG. 3, the vertical distance along the optical axis from objective lens 6 to reflection mirror 11 is $V_{x1}$, the vertical distance along the optical axis from reflection mirror 11 to lens 31 is $V_{x2}$, the horizontal distance from reflection mirror 11 to the optical axis of excitation light 61 from light source 60 is $H_{x1}$, and the horizontal distance from the optical axis of excitation light 61 to the optical axis position of folding-back at corner mirror 21 is $H_{x2}$.

The above described telecentric distance L is therefore expressed as shown in equation (1), $$L = V_{x1} + V_{x2} + H_{x1} + 2 \times H_{x2} \tag{1}$$

and stages 10 and 20 are moved, with this distance L being kept constant.

Then, let C be $$C = L - V_{x1} - V_{x2},$$

and equation (2) is obtained.

$$C = H_{x1} + 2 \times H_{x2} \tag{2}$$

Consequently, when first stage 10 is moved so that the distance $H_{x1}$ takes the value "$H_{x1}$" to move objective lens 6 to a position corresponding to a sample, second stage 20 is moved so that the following equation holds:

$$H_{x2} = (C - H_{x1})/2$$

This enables telecentric distance L to be kept constant.

As described above, by moving stages 10 and 20 appropriately, samples in each concave part 2 of micro titer plate 1 can be observed in turn. In this case, there is no danger of solutions sloshing out of each concave part 2 as experienced in the past. In addition, since stages 10 and 20 are smaller and lighter than micro titer plate 1, they can be easily moved at a high speed.

Further, the moving directions of stages 10 and 20 are not restricted only to a horizontal direction (X direction) parallel to the paper surface as shown in FIG. 4(a), but the stages may also be moved in the Y direction orthogonal to the X direction as shown in FIG. 4(b). Of course, the telecentric distance must be kept constant in this case.

In detail, in this case, it is sufficient to use both X direction correcting stage of 20x and Y direction correcting stage of 20y for the above purpose. These two stages are coordinated to perform correcting actions so that the total optical distance along the optical axes remains constant.

Figure 5A:
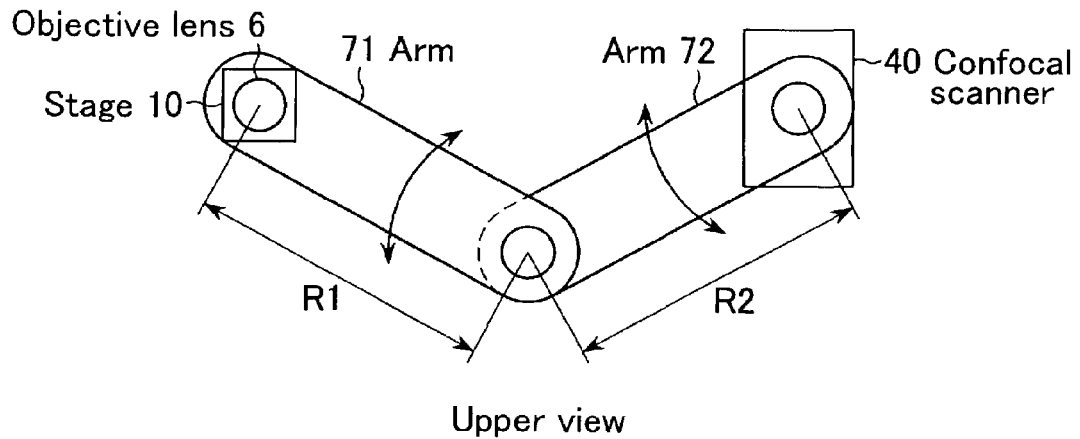
FIG. 5 is a configuration drawing indicating another embodiment of the stage-drive.
Figure 5B:
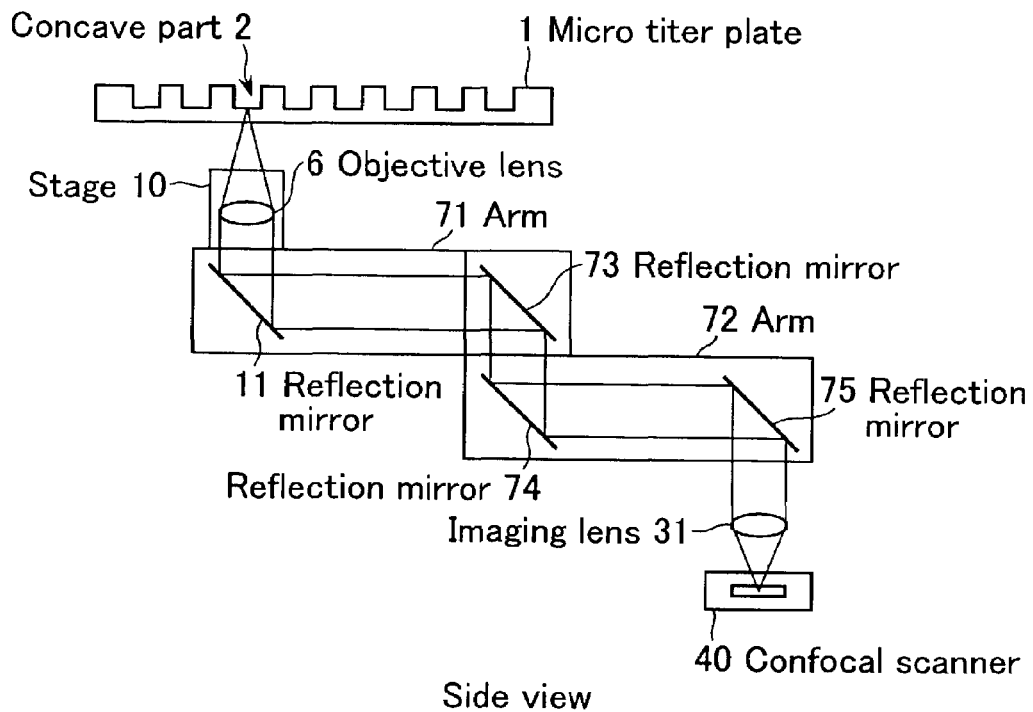

Furthermore, as shown in the top view of FIG. 5(a) and in the side view of FIG. 5(b), the objective lens may also be appropriately moved in the X and Y directions to the photo-detecting part by controlling the turning angles of arms 71 and 72 which are linked and supported with shafts respectively. In this case, the telecentric distance is kept constant because the horizontal distance R1+R2 is constant.

In addition, any of mechanisms adopted in a linear motor, a rack-and-pinion, screws, a planar servomotor, ball screws, a direct-drive motor, etc. can be utilized as the moving mechanism of stages 10 and 20.

The photo-detecting means that detects the sample image may also be not only a confocal scanner but an ordinary camera.

In the case of obtaining a sample image, that image is not restricted to a fluorescence image in the reflection type mechanism but can also be a transmission image in a transmission type mechanism in which each constituent means on the light source side and that on the light detecting side are arranged counter to each other with micro titer plate 1 between.

Figure 6:
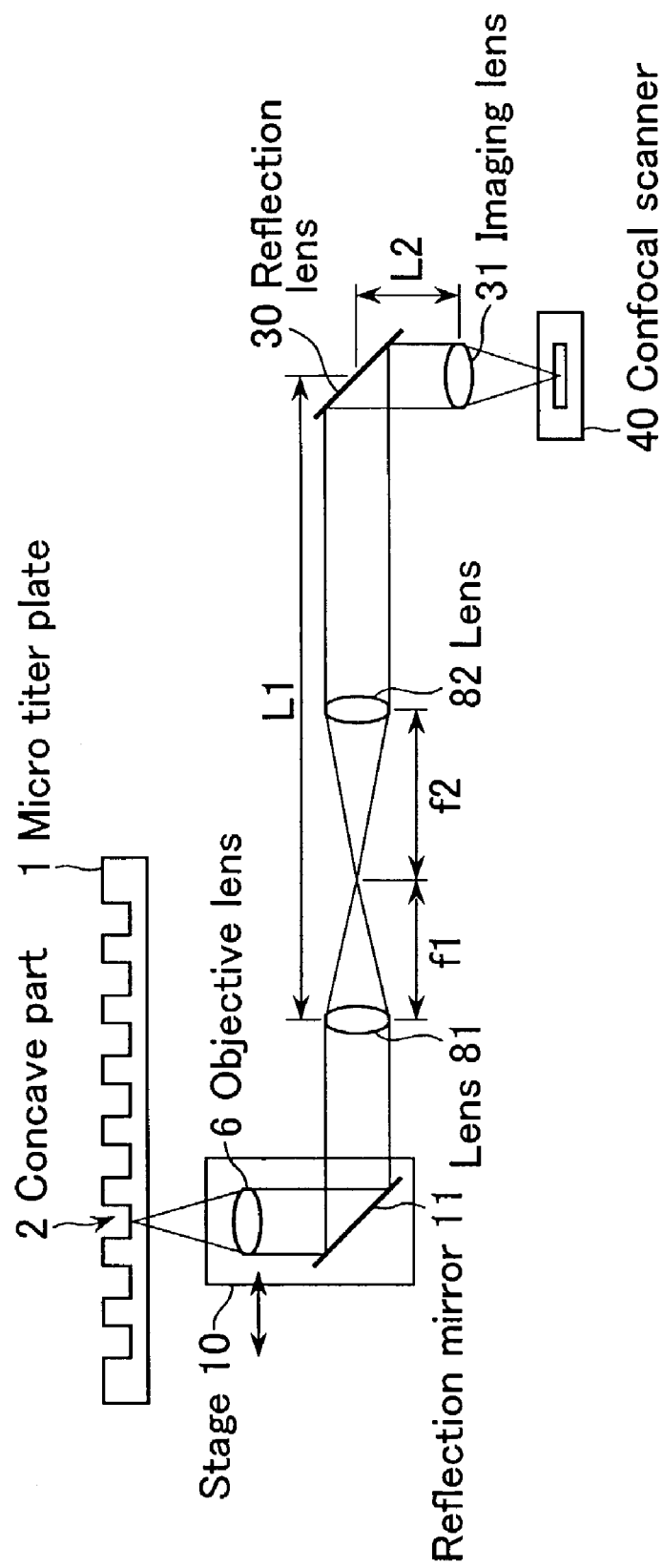
FIG. 6 is a drawing showing another different embodiment of the present invention.

FIG. 6 is a drawing showing an embodiment in the case of the intermediate relay lens method. The return light from the sample is transmitted through objective lens 6 and reflected by reflection mirror 11, then transmitted through lenses 81 and 82, reflected by reflection mirror 30, and incident to confocal scanner 40 after focused with imaging lens 31. Lenses 81 and 82, if focal lengths of each lens are assumed to be f1 and f2 respectively, are located apart from each other by a distance of (f1+f2).

Let the distance from lens 81 to reflection mirror 30 along the optical axis be L1, and the distance from reflection mirror 30 to lens 31 along the optical axis be L2, and keep the distance along the optical axis of (L1+L2) (=L) constant. If the distance along the optical axis of (L1+L2=L) is sufficiently long against the moving distance of objective lens 6, the above described light quantity shortage at the periphery of an image becomes a negligible amount. Thus, if reduction of light quantity on the periphery is up to approximately ten percent, correction of light quantity is either not necessary or can be carried out easily.

Accordingly, a wide variety of samples can be measured by being scanned at a high speed without shortage of light quantity on the image periphery, by the movement only of objective lens 6. In addition, if a mechanism to change the direction of the optical axis is adopted as shown in FIG. 4, the measurement system can compensate the movement of objective lens 6 not only in the X direction but also in the Y direction.

As described above, the present invention has the following effects:

(1) Since the system is constructed in such a way as to fix the micro titer plate and to move the objective lens, sloshing-out of solutions from the concave parts of the micro titer plate as seen in conventional systems can easily be prevented.

(2) Since the weight of the objective lens is minor compared with that of the photo-detecting parts such as the micro titer plate or the confocal scanner, the speed of movement of the objective lens to positions corresponding to samples can easily be increased.

(3) Since the above described objective lens is moved with the telecentric distance kept constant, light quantity shortage on the periphery of the screen does not occur.

(4) In using the intermediate relay lens system, light quantity shortage on the periphery of the screen essentially does not occur in a manner similar to the above because the distance along the optical axis in the intermediate relay lens part is sufficiently longer than the objective lens moving distance.

What is claimed is:

1. A measurement system that optically measures a plurality of samples arranged in an array in turn via an objective lens and an imaging lens, comprising:

an actuator means that moves the objective lens to a position corresponding to each of the samples;

a photo-detecting part that detects a sample image via the objective lens and imaging lens, and an actuator means for optical path length correction to keep the telecentric distance between said objective lens and said imaging lens constant when said objective lens is moved, wherein said array and said imaging lens are fixed, and wherein said actuator means for optical path length correction moves a second stage including a corner mirror in two-dimensional directions in a plane parallel with a plurality of samples arranged in the array.

2. A measurement system that optically measures a plurality of samples arranged in an array in turn via an objective lens and an imaging lens, comprising:

an actuator means that moves the objective lens to a position corresponding to each of the samples;

an actuator means for optical path length correction to keep the telecentric distance between said objective lens and said imaging lens constant when said objective lens is moved, and a photo-detecting part that detects a sample image via the objective lens and imaging lens, wherein said array is fixed, and wherein said actuator means for optical path length correction includes a corner mirror.

3. A measurement system in accordance with claim 2, further comprising an intermediate relay lens part for prolonging the optical path length between said objective lens and said imaging lens, wherein a light quantity shortage on the periphery of the image due to movement of the objective lens does not occur.

4. A measurement system in accordance with claim 2, wherein said actuator means and said actuator means for optical path length correction move respectively a first stage including said objective lens and a second stage including said corner mirror in two-dimensional directions in a plane parallel with a plurality of samples arranged in the array.

5. A measurement system in accordance with claim 2, wherein said actuator means moves a first stage including said objective lens in two-dimensional directions in a plane parallel with a plurality of samples arranged in the array.

6. A measurement system in accordance with claim 2, wherein said actuator means for optical path length correction moves a second stage including a corner mirror in two-dimensional directions in a plane parallel with a plurality of samples arranged in the array.

7. A measurement system in accordance with claim 2 or 4, wherein said photo-detecting part includes a confocal scanner or a camera.

8. A measurement system in accordance with claim 2 or 4, wherein at least either one of said actuator means or said actuator means for optical path length correction includes a moving means using at least one of a linear motor, a planar servomotor, a rack-and-pinion, screws, ball screws, and a direct drive motor.

9. A measurement system in accordance with claim 7, wherein at least either one of said actuator means or said actuator means for optical path length correction includes a moving means using at least one of a linear motor, a planar servomotor, a rack-and-pinion, screws, ball screws, and a direct drive motor.

* * * * *